United States Patent [19]

Ballester-Rodes et al.

[11] Patent Number: 5,021,582
[45] Date of Patent: Jun. 4, 1991

[54] FAMOTIDINE POLYMORPHIC FORMS AND THEIR PREPARATION PROCESS

[75] Inventors: Montserrat Ballester-Rodes; Francisco E. Palomo-Nicolau; Antonio L. Palomo-Coli, all of Barcelona, Spain

[73] Assignee: Centro Marga Para La Investigacion S.A., Barcelone, Spain

[21] Appl. No.: 197,329

[22] Filed: May 23, 1988

[30] Foreign Application Priority Data

Jun. 22, 1987 [ES] Spain .................................. 8702020
Oct. 29, 1987 [ES] Spain .................................. 8703326
Mar. 23, 1988 [ES] Spain .................................. 8800888

[51] Int. Cl.$^5$ .......................................... C07D 277/48
[52] U.S. Cl. ................................................. 548/197
[58] Field of Search ...................................... 548/197

[56] References Cited

U.S. PATENT DOCUMENTS 4,496,737  1/1985  Hoffman ......................... 548/193
4,894,459  1/1990  Bod ................................. 548/197

FOREIGN PATENT DOCUMENTS 0256747  2/1988  European Pat. Off. ............ 548/197
 256747  2/1988  European Pat. Off. ............ 548/193
3644246  12/1987  Fed. Rep. of Germany ...... 548/193
2180237  3/1987  United Kingdom ................ 548/193

OTHER PUBLICATIONS

O.G. U.S. P.T.O. 1-16-90, p. 1411.
Haleblian, J. Pharm. Science, 58, 911, (1969).

Primary Examiner—Robert Gerstl
Attorney, Agent, or Firm—Fleit, Jacobson, Cohn, Price, Holman & Stern

[57] ABSTRACT

It is described the preparation of the famotidine polymorphs with low melting point and relative high or low apparent densities. They differ from the polymorph of high melting point and high density, in the physical-chemical and biological properties, of interest in galenic formulations and preparation of the drug.

3 Claims, No Drawings

FAMOTIDINE POLYMORPHIC FORMS AND THEIR PREPARATION PROCESS

DESCRIPTION

Famotidine is a generic term used to identify the chemical compound N-sulfamoyl-3-(2-guanidinothiazol-4-yl)methylthiopropionamidine:

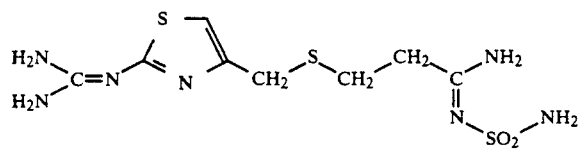

This compound is active to inhibit the secretion of acid and pepsin being used for the treatment of the gastric and duodenal ulcer, as in the Zolliger-Ellison syndrome, among other affections of the upper digestive apparatus.

The famotidine is a $H_2$-receptor antagonist produced by synthesis. In the patent GB No. 2055800 A, a process is described where 3-[(2-guanidinothiazol-4-yl)methylthio] propionimidate is reacted with sulfamide and the evaporated liquids yield a residue which is purified by chromatography, passing in solution through a silica gel column, isolating a product with m.p.: 163°–164° C. In the U.S. Pat. No. 4,496,737, from the resulting solution of the reaction of N-sulfamylacrylamidine with 2-guanidinothiazol-4-methylthiol generated "in situ", the solvent (aqueous-methanol) is evaporated and the residue is passed in solution through a silica gel column yielding a product with m.p.: 160° C. In both cases the eluent used is a mixture of methanol-chloroform.

The patent EP No. 0128736, describes a process of famotidine preparation, obtaining a product with m.p.=163°–164° C., that is obtained by precipitation from its aqueous solution as acetate, by means of sodium hydroxide solution. With this method famotidine, proceeding from the raw reaction product, is purified with m.p.=157.6° C.

The scant solubility of famotidine in methanol (0.5–1.0%), still minor in the presence of chloroform, makes this purification and isolation process industrially impracticable. From recrystallization in other organic solvents, dimethylformamide, dimethylacetamide, dimethylsulfoxide or acetonitrile, either by dilution with water or preferably with dichloromethane or chloroform, it results a product of variable melting point, with an interval of 164°–176° C. The microscopic observation reveals a conglomerate in the shape of concretions.

The famotidine hydrochloride is very little soluble in water, and the aqueous suspension adjusted at pH=7,0–7,5 yields famotidine with an aspect of granular concretions and presents an interval of melting point between 158° and 172° C.

These variations in the thermic properties and the different infrared spectrums for the product with the same chemical structural form, reveal the presence of polymorphic forms, associated to different physical forms, with characteristic properties of the crystalline structure, which are related with the material purity, the apparent density and the activity. Consequently, it is interesting to dispose of the polymorphic form with specific characteristics the more favorable for pharmaceutical uses.

We have discovered now a crystalline famotidine, having specific properties, desirable for pharmaceutical and medical purposes. A polymorph is presented in the shape of concretions with a high melting point and high apparent density (from now on CMI-AA). Another polymorph with a low melting point is associated to the crystalline forms of high and low apparent densities, in limit forms (from now on CMI-BA and CMI-BB respectively). These are obtained by precipitation or crystallization of the solution of famotidine in methanol, prepared from the famotidine hydrochloride and being liberated by means of a tertiary organic base. By means of that process, all the forms are convertible into the CMI-BB polymorph, its formation being favored by inoculating with the corresponding crystal. They differ between them by their physical-chemical properties and bioactive behavior.

A new crystalline form of famotidine is described and claimed herein, having the following unique X-Ray diffraction properties at $\lambda=1.5405$ Å using a radiation source of Cu, 40 kw and 20 ma, coming from a Siemens Kristalloflex 810 Interface DACO-MP equipment:

| High density Famotidine CMI-BA | | Low density Famotidine CMI-BB | |
|---|---|---|---|
| d: | I/I1 | d: | I/I1 |
| 15.93 | 0.13 | 14.68 | 0.28 |
| 14.75 | 0.51 | 7.62 | 0.58 |
| 7.62 | 0.47 | 7.15 | 0.14 |
| 5.87 | 0.18 | 5.87 | 0.12 |
| 5.62 | 0.45 | 5.61 | 0.41 |
| 5.03 | 0.35 | 5.03 | 0.20 |
| 4.92 | 0.56 | 4.92 | 0.38 |
| 4.57 | 0.44 | 4.57 | 0.41 |
| 4.42 | 0.92 | 4.42 | 1.00 |
| 4.31 | 0.22 | 4.31 | 0.20 |
| 4.25 | 0.65 | 4.25 | 0.64 |
| 3.96 | 0.84 | 3.95 | 0.52 |
| 3.89 | 0.61 | 3.89 | 0.41 |
| 3.81 | 0.27 | 3.81 | 0.32 |
| 3.76 | 0.12 | 3.69 | 0.68 |
| 3.69 | 1.00 | 3.61 | 0.33 |
| 3.62 | 0.54 | 3.47 | 0.09 |
| 3.47 | 0.11 | 3.40 | 0.19 |
| 3.40 | 0.26 | 3.37 | 0.20 |
| 3.37 | 0.25 | 3.27 | 0.21 |
| 3.27 | 0.19 | 3.18 | 0.06 |
| 3.18 | 0.07 | 3.09 | 0.08 |
| 3.10 | 0.11 | 2.95 | 0.28 |
| 3.02 | 0.04 | 2.91 | 0.12 |
| 2.95 | 0.31 | 2.85 | 0.13 |
| 2.91 | 0.14 | 2.77 | 0.36 |
| 2.85 | 0.10 | 2.72 | 0.05 |
| 2.77 | 0.30 | 2.62 | 0.06 |
| 2.73 | 0.06 | 2.53 | 0.19 |
| 2.62 | 0.07 | 2.50 | 0.14 |
| 2.54 | 0.17 | 2.46 | 0.07 |
| 2.50 | 0.16 | 2.42 | 0.07 |
| 2.48 | 0.10 | 2.40 | 0.09 |
| 2.46 | 0.09 | 2.29 | 0.10 |
| 2.43 | 0.08 | 2.23 | 0.06 |
| 2.35 | 0.06 | 2.20 | 0.11 |
| 2.21 | 0.09 | 2.17 | 0.07 |
| 2.15 | 0.11 | 2.15 | 0.12 |
| 2.11 | 0.09 | 2.12 | 0.06 |
| 2.09 | 0.06 | 2.11 | 0.11 |
| 2.04 | 0.07 | 2.03 | 0.08 |
| 1.97 | 0.06 | 1.97 | 0.07 |
| 1.83 | 0.07 | 1.85 | 0.05 |
| 1.78 | 0.07 | 1.83 | 0.06 |
| 1.76 | 0.37 | 1.79 | 0.06 |
| 1.74 | 0.08 | 1.76 | 0.06 |
| 1.73 | 0.10 | 1.74 | 0.07 |
| 1.70 | 0.05 | 1.70 | 0.05 |
| 1.60 | 0.30 | 1.61 | 0.05 |

| High density Famotidine CMI-BA | Low density Famotidine CMI-BB |
|---|---|
| 1.50 ... 0.05 | 1.60 ... 0.13 |

The polymorphic form presents a crystalline structure of high density and another of low density, respectively in the form of crystals with the appearance of big acicular prisms and extremely dense, or with the appearance of very little dense, short and diminutive acicular prisms. The term "high density" means that the apparent density is higher than 0.55 g/ml, preferably with a range of 0.70 to 0.80 g/ml; "low density" expresses that the preferable value comprises a range between 0.20 and 0.30 g/ml. These materials do not present static charges and their characteristics make possible the direct use in some operations of pharmaceutical formulations.

The new crystalline composition of this invention can be obtained from famotidine, whatever the synthesis sequence is, with a melting point comprised in the interval of 160° to 180° C. and infrared spectrum that shows a different structural behavior. The process, which comprises hydrochloride, hydrobromide, sulfate, nitrate or phosphate salt of famotidine consists in:

(1) suspension of a form of the $H_2$-receptor antagonist in methanol, (2) addition of the stoichiometric quantity of a strong acid and enough to obtain a solution, (3) at the temperature of 0° C. to 25° C., add an organic base which salt of the strong acid is soluble in methanol, (4) increase the temperature till obtain a solution, (5) dilute with a miscible solvent as the dichloromethane or the chloroform, (6) optionally inoculate with crystals of high density and cool at 0°-10° C. and (7) isolate the crystalline compound by filtration, decantation or similar methods.

It is important, that if in the prior process the addition of the organic base is realized gradually and slowly, the precipitation begins at pH near to 2.0 and even if it ends at pH=6.5-7.0, a product is isolated with m.p.=186°-188° C. This product suspended in water and under agitation at pH=7.0-7.5 yields a mixture of polymorphs with m.p. =165°-173° C. Consequently, to obtain the low density polymorph, it is necessary to realize quickly the addition of the organic base.

An alternative preparation of the high density polymorph, comprises the inoculation with high density crystals, leaving the solution at rest at the temperature of 10°-15° C.

Mixtures of polymorphs with m.p.=172°-174° C. or 169°-172° C. are isolated from the acetonitrile or dimethylformamide, by addition of a little portion of water and cooling between 0° and 10° C. Mixtures are also originated with m.p. from 150° to 168° C., when the solution of the famotidine hydrochloride in methanol is diluted with dichloromethane and afterwards is brought to a slightly alkaline pH with an organic base.

The polymorph with m.p.=159°-161° C. (FIG. 1) is obtained from the solutions of the famotidine hydrochloride in methanol, adjusted at slightly alkaline pH and the precipitate so formed is dissolved again by heating. The solution obtained, is diluted with dichloromethane and left some time at the temperature of 10°-15° C.

For the purposes of the invention are adequate the organic bases diethylamine, dipropylamine, triethylamine, N-ethylpiperidine, N-methylmorpholine, N-tripropylamine, and the bicyclic amidines 1,8-diazabicyclo[5.4.0]undec-7-ene (DBU), 1,5-diazabicyclo[4.3.0]-non-5-ene (DBN) and generally organic bases which hydrochloride salts may be soluble in methanol, dichloromethane and mixtures of both.

Depending on the selection of the solvent to obtain the hydrochloride solution, the temperature and the chlorinated solvent, dichloromethane or chloroform, the low melting point polymorph is isolated, showing two different apparent densities. The high density polymorph with m.p.= 159°-161° C. and the polymorph of low density with m.p.=157°-159° C. show identical infrared and ultraviolet spectrums, with sensible differences in the X-Ray diffraction properties.

The dichloromethane, the chloroform and the trichloroethylene result to be selective for the obtention of the polymorph, with a high or a low apparent density that comprises the values near to 0.80 and 0.20 respectively.

Now, it has been verified the importance of the conversion of any polymorph or its mixtures into the polymorph CMI-BB, that has showed (a) more purity, (b) more physical-chemical stability and (c) more bioactivity than that observed in the other forms.

Are important a higher purity and an excellent stability, that in some way stop the possible processes of degradation with respect to the time. However, it has turned out to be surprising the higher biological activity of the CMI-BB polymorph. This compound (table 1, C) withstands a pressure of 5-10 tons, being transformed in a white powder with amorphous appearance, without experimenting variation in the melting point. On the other hand a sensitive variation in the melting point (CMI-MB), particularly using classical crystallization procedures and having relative low apparent density, presents an interval that reaches 164° C. by uncontrol of the crystallization.

With the aim of improving the conditions of the preparation process of the product CMI-BB, it has been established that an object of the invention consists in inducing the crystallization, from the famotidine solution, by inoculation. For that, the solution is inoculated at the desired temperature, preferably between 50° and 30° C.

The influence of the dilution of the medium is reflected also in the relative apparent density of the desired product CMI-BB. That is why, before proceeding to the incorporation of the crystal, the dilution of the solution is realized by the addition of a solvent preferably chlorinated. Among them, are selected dichloromethane, chloroform, carbon tetrachloride, 1,2-dichloroethane, trichloroethylene and polychloroethanes among others.

The system alcohol-diluent of election, is related to the highest solubility of the salt of the organic base employed, to form the solution of famotidine in methanol, ethanol or isopropanol.

The famotidine polymorph CMI-BB obtained by means of the fast crystallization system, has been object of a comparative study for the bioactive behavior, in front of the other forms.

The study of the antiulcerous activity of the polymorphs has been realized in lots of male Wistar rats, with weights comprised between 202 and 203 g, distributed in six groups of treatment indicated in the following table 1:

TABLE 1

| GROUP | TREATMENT | MP (°C.) | AD (R) | DOSE (mg/Kg; p.o.) |
|---|---|---|---|---|
| A | control | — | — | — |
| B | Cimetidine (Reference) | — | — | 100 |
| C | CMI-BB | 158–160 | 0.20 | 6 |
| D | CMI-MB | 160–163 | 0.28 | 6 |
| E | CMI-BA | 158–161 | 0.77 | 6 |
| F | CMI-AA | 167–170 | 0.78 | 6 |

In a solution of carboxymethylcellulose (0.5%) in distilled water were suspended the substances for the treatment; this was administered in a volume of 10 ml/Kg, p.o.

The ulcerogenic agent, indomethacin, was applied 30 min. after the administration of the respective treatments (30 mg/10 ml/Kg, p.o.) and the animals were sacrificed 6 hours later. The stomachs were extracted and the gastric lesions produced evaluated in millimeters of length (mm).

The antiulcerous activity of the tested drugs, was evaluated by inhibition percentage calculated from the average length of each treated group and the average of the control group. The results obtained in the different groups were compared statistically by means of the correlation analysis and the Duncan-Kramer test. The results are summarized in table 2.

There are important significant activity differences among the different polymorphs, being surprising the results between the extreme groups B and F (table 2).

The polymorph of low melting point (C) showed a 30% more of activity than the high melting point one (F). On the other hand, the results show significative differences depending on the apparent relative density of the product (tables 1 and 2).

Therefore, the polymorph CMI-BB is the preferred one for a therapeutic use in Medicine, and in pharmaceutical formulations, particularly those that do not modify the crystalline structure. Also the composition of its non-toxic salts of inorganic and organic acids and aminoacids that do not alter their polymorphism.

C., ending at 172° C. The microscope observation shows the majority formation of concretions. I.R. (KBr) $\nu$ cm$^{-1}$: 3400, 3300, 3220 (sh), 3100, 2880, 1685, 1650 (m), 1600 and 1550.

B. To the suspension of famotidine (3,0 g, m.p. = 155°–161° C.) in methanol (15,0 ml) concentrated hydrogen chloride (1.86 ml, 35%) is added, resulting a colorless solution and a temperature of 33° C. at pH = 1.0. It cools down at 0°–5° C. (in about 10–15 min.) and the addition of triethylamine (2.5 ml) is brought out gradually, controlling the pH1.8–2.0, beginning the precipitation. In the course of about 30 min., pH remains at 2.0, reaching finally the pH = 6.5. The precipitate filtered, washed with methanol, dichloromethane, and dried yields 2.59 g of product with m.p. = 186°–188° C. I.R. (KBr) $\nu$ cm$^{-1}$: 3420 (sh,s), 3300, 3220 (m), 3170 (m), 3100 (m), 2980, 2890, 1675, 1650 (w), 1610 y 1560.

This product, suspended again in methanol and stirred during some time (15 min.) with trimethylamine at pH = 7.5, yields a mixture of polymorphs with m.p. = 165°–173° C. The X-Ray diffraction properties are different and distinguishable from the corresponding to the forms crystallized in high and low density prisms.

EXAMPLE 2

High density polymorph

To the famotidine suspension (100.0 g.; IR(KBr) $\nu$ cm$^{-1}$: 3430 and 3380(duplet,s), 3300(s), 3220(s), 1660 and 1635(duplet,s), 1600(s) and 1535(s)) in methanol (1500 ml), under agitation, concentrated hydrogen chloride (35%, density 1.18; 60.0 ml, 70.8 cmol approximately) is added, and to the resulting solution triethylamine (100.0 ml; 71.0 cmol) is added, been able to cause a solution momentarily, with elevation of the temperature of the mass (interval 25°–35° C.), causing finally a precipitate. The mixture is heated at beginning of boiling (63° C.). To the resulting solution (without heating), dichloromethane (3000 ml) is gradually added and it is left at rest at the temperature of 10°–15° C. during three to four hours.

TABLE 2

FAMOTIDINE POLYMORPHICS: ANTIULCER ACTIVITY

| GROUP | TREATMENT (Drug) | DOSE (mg/Kg; p.o.) | WEIGHT (g) (Med ± EE) | ULCERS (mm) (Med ± EE) | INHIBITION (% respect to control) |
|---|---|---|---|---|---|
| A | Control | — | 218,7 ± 2,84 | 70,5 ± 7,89 | — |
| B | Cimetidine[a] | 100 | 212,8 ± 2,02 | 7,0 ± 2,33 | 90,0 |
| C | CMI-BB | 6 | 212,6 ± 2,20 | 0 | 100,0 |
| D | CMI-MB | 6 | 218,4 ± 1,95 | 2,5 ± 1,12 | 96.4 |
| E | CMI-BA | 6 | 214,2 ± 1,94 | 13,2 ± 4,77 | 81,3 |
| F | CMI-AA | 6 | 211,8 ± 2,22 | 22,0 ± 5,17 | 68,8 |

Famotidines: CMI protocol. Average - standard error (n = 10). Statisticly significant differences p < 0,05 (Duncan-kramer test).
[a]Reference.

EXAMPLE 1

Polymorphs mixture

A. To the suspension of the famotidine (3,0 g, m.p.: 173°–176° C) in water (15 ml), concentrated hydrogen chloride (1.86 ml, 35,0%) is added, causing a thick white mass of the famotidine hydrochloride. Cooled in water-ice bath, it is adjusted with triethylamine (2.5 ml) at pH = 7.0–7.5 and stirred during 60 min. The white precipitate is filtered, washed with water and methanol. Once dried, it yields 2.03 g of famotidine which presents the beginning of melting at 158° C. remaining stationary at this temperature, and afterwards continues up to 166°

The precipitate is isolated by filtration, washed with methanol and dichloromethane, yielding 75.0 g. of the title's compound with m.p.: 159°–161° C., apparent density 0.55, infrared spectrum FIG. 1, crystals FIG. 2.

The observation with a stereoscopic microscope, Kiowa SDZ-PL model provided with zoom, shows long acicular prisms in an homogeneous mixture and of white color. The melting point is given without being corrected and was determined in a binocular microscope Reichert Thermovar.

From the mother liquors, by the usual methods, the solvents and 10.0 to 15.0 g more of famotidine are recovered.

EXAMPLE 3

Low density polymorph

Famotidine is suspended (143.0 g; IR(KBr) $\nu$ cm$^{-1}$: 3430 and 3380 (duplet,s), 3300(s), 3220(s), 1660 and 1635(duplet,s), 1600(s) and 1535(s)) in methanol (2000 ml) and controlling the internal temperature of 20°-22° C., concentrated hydrogen chloride (35.0%, 85.0 ml) is added. To the resulting solution, bicyclic amidine DBU (147,5 g) is added all at once, reaching about 35° C. After some time (approximately 10–15 min.), it becomes turbid. Immediately it is heated at reflux temperature, obtaining a colorless solution at the temperature of about 50°-55° C. It is diluted with chloroform (5000 ml) and at about 35°-36° C. the precipitation begins. After cooling three hours at 10°-15° C., it is filtered, washed successively with methanol, dichloromethane and dried, resulting 107.2 g of the title's compound, with m.p.: 159°-161° C., apparent density =0.20, infrared spectrum identical as the one of FIG. 1, crystals FIG. 3.

The observation by stereoscopic microscope Kiowa SDZ-PL model provided with Zoom, shows short prisms, in homogeneous mixture and of snowy white color.

The recuperation of solvents is realized by the usual methods. From the distillation residue are obtained 25.0 g. more of compound, which is recycled in the conversion process.

EXAMPLE 4

High density polymorph (CMI-BA)

Following the second example and substituting the triethylamine by DBN, the title's compound is obtained with similar yield and identical characteristics.

EXAMPLE 5

Low density polymorph (CMI-BB)

Following the third example and substituting the DBU by N-methylmorpholine, it is obtained the title's compound with a similar yield and identical characteristics.

EXAMPLE 6

High density polymorph (CMI-BA)

Following the second example and adjusting suitably the methanol and dichloromethane quantity, the triethylamine is substituted by one of the following organic bases: N-ethylpiperidine, N-tripropylamine, N-tributylamine, diethylamine, dipropylamine, N-propylamine, to obtain the title's compound with a similar yield and identical physical-chemical characteristics.

EXAMPLE 7

Low density polymorph (CMI-BB)

Famotidine (m.p.: 167.5°-169.5° C., apparent density (0.78; 150.0 g) in methanol (2250 ml), is dissolved by means of hydrogen chloride (35.0%; 90 ml) and by addition of triethylamine (155.0 ml), the possible precipitate is dissolved again heating at reflux. To the solution, at hot temperature is added methylene chloride (2000 ml), causing precipitation. After 4 hours (5°-10° C.), are isolated 113.6 g of the title's compound with m.p.: 157°-159° C. and apparent density=0.29. Infrared spectrum identical to the one of FIG. 1 and crystals like the ones of FIG. 3.

EXAMPLE 8

High density polymorph (CMI-BA)

Following the prior example, using famotidine of the same characteristics, dichloromethane (1000 ml) is added and the resulting solution is left at the temperature of 0°- 5° C. (10 h.). It results 117.0 g of the title's compound with a m.p.=158°-160.5° C., apparent density=0.69. Identical infrared spectrum to the one of FIG. 1 and the crystals as the ones of FIG. 2.

EXAMPLE 9

Low density polymorph (CMI-BB)

Famotidine is suspended (7.5 g; m.p.: 173°-176° C., physical form=concretions), in methanol (30 ml). By addition of concentrated hydrogen chloride acid (4.65 ml; 35.0%), it results immediately a colorless solution. Cooling in water-ice bath (0°-5° C.), triethylamine (6.25 ml) is added all at once, controlling the pH=7.5. It begins an abundant and quick precipitation of white product. After some time (30 min.) under agitation, it is filtered, washed with methanol and later with dichloromethane. Once dried, it yields 6.16 g of famotidine with m.p.=155°-161° C. This product is suspended in methanol and with triethylamine is adjusted to pH=7.0-7.5, stirring the suspension during some time (15 min.). Washed and dried, it yields product with m.p.=159°-161° C., apparent density 0.20 to 0.22 g/ml and the microscopic observation shows conglomerates formed by diminutive crystals. IR and UV spectrums identical to the ones of the high density polymorphic form.

EXAMPLE 10

Low density polymorph (CMI-BB)

Instead of the famotidine, it is used famotidine hydrochloride isolated by filtration of the precipitate which is produced in the procedure of example 1A. Following the previous example, famotidine is obtained with identical result.

EXAMPLE 11

High density polymorph (CMI-BA, with inoculation)

To the suspension of famotidine (300.0 g) in methanol (4500 ml), it is added concentrated hydrogen chloride (180 ml, 35%) resulting a complete solution. Afterwards triethylamine (310,0 ml) is added and it is heated at reflux temperature obtaining a colorless solution. At hot temperature, chloroform (2000 ml) is added and, after cooling down, at the temperature of 10° to 15° C., it is inoculated with high density famotidine. The solution is left at rest at 4°-5° C. overnight. After filtration and washing with methanol and dichloromethane, 255.2 g of product are isolated in the shape of big acicular prisms, with an apparent density of 0.77 to 0.80 g/ml, m.p.=158°-161° C., I.R. and U.V. spectrums correct and X-Ray diffraction properties expressed in the present invention.

EXAMPLE 12

Low density polymorph (CMI-BB, with inoculation)

Following example 3, DBU (144 ml) is added and the solution obtained by heating at reflux temperature is diluted with chloroform and immediately it is inoculated with CMI-BB. Next, the procedure is exactly as expressed in the mentioned example 3, obtaining the title's compound with similar results.

Proceeding exactly and substituting chloroform by the same amount of 1,2-dichloroethane or trichloroethylene, the title's compound is obtained with 89,4% yield, m.p.=151°-154° C., I.R. spectrum FIG. 1 and apparent density approximately 0,21-0,22.

EXAMPLE 13

Low density polymorph (CMI-BB, with inoculation)

Following example 2 or example 11, the hot solution, diluted with the chlorinated solvent, is inoculated with CMI-BB and the formation of crystals is produced, that correspond to the title's compound, which is isolated with virtually identical yield and characteristics.

I claim:

1. A process for preparing famotidine polymorphs, comprising the steps of:
   adding an acid to a suspension of famotidine in a C1-C3 alcohol to produce to a solution, said acid being selected from the group consisting of hydrogen chloride, hydrogen bromide, sulfuric acid, nitric acid and phosphoric acid;
   reacting said solution with a tertiary organic base or a bicyclic amidine selected from the group consisting of 1,8-diazabicyclo [5.4.0]undec-7-ene and 1,5-diazabicyclo [4.3.0]non-5-ene, thereby forming a precipitate;
   redissolving said precipitate by heating the solution containing the precipitate at a temperature between 50° and 650° C., thereby producing an alcoholic solution;
   diluting said alcoholic solution with a chlorinated hydrocarbon selected from the group consisting of dichloromethane, chloroform, carbon tetrachloride, 1,2-dichloroethane and trichloroethylene; and then
   recovering a famotidine polymorph of low apparent density and low melting point from the diluted alcoholic solution by precipitation or crystallization under cooling at 0°-5° C. and isolation by filtration at a temperature between 0° and 15° C.

2. A process according to claim 1, wherein the tertiary organic base together with the acid of the salt of famotidine forms a second salt which is soluble in methanol or in a mixture of methanol with a chlorinated solvent.

3. A process according to claim 1 for the preparation of the famotidine polymorph CMI-BB with low apparent density and low melting point, wherein said famotidine is selected from the group consisting of famotidine polymorphs having a high melting point, famotidine polymorphs having a high apparent density and mixtures thereof, said alcohol is methanol, said inorganic acid is hydrogen chloride, and said organic base is 1,8-diazobicyclo [5.4.0]undec-7-ene, and wherein the methanol solution diluted with the chlorinated solvent is inoculated with a germ of famotidine of low melting point and relative low apparent density, whereby precipitation of the famotidine polymorph CMI-BB is initiated at a temperature between 30° and 50° C.

* * * * *